US010309890B2

(12) United States Patent
Wang et al.

(10) Patent No.: US 10,309,890 B2
(45) Date of Patent: Jun. 4, 2019

(54) METHOD TO MEASURE A MOLECULAR DIFFUSION COEFFICIENT IN A POROUS POWDER

(71) Applicants: Fei Wang, Beijing (CN); Dezheng Wang, Beijing (CN); Yao Wang, Beijing (CN)

(72) Inventors: Fei Wang, Beijing (CN); Dezheng Wang, Beijing (CN); Yao Wang, Beijing (CN)

(*) Notice: Subject to any disclaimer, the term of this patent is extended or adjusted under 35 U.S.C. 154(b) by 0 days.

(21) Appl. No.: 15/438,795

(22) Filed: Feb. 22, 2017

(65) Prior Publication Data

US 2017/0160184 A1  Jun. 8, 2017

Related U.S. Application Data

(62) Division of application No. 14/530,754, filed on Nov. 2, 2014, now Pat. No. 9,719,909.

(30) Foreign Application Priority Data

Sep. 29, 2014 (CN) .......................... 2014 1 0515969

(51) Int. Cl.
*G01N 15/08* (2006.01)
*G01N 33/00* (2006.01)

(52) U.S. Cl.
CPC ......... *G01N 15/0826* (2013.01); *G01N 33/00* (2013.01); *G01N 2033/0091* (2013.01)

(58) Field of Classification Search
CPC .................................................. G01N 15/0826
See application file for complete search history.

(56) References Cited

U.S. PATENT DOCUMENTS

2004/0134258 A1* 7/2004 Wang ....................... G01N 7/04
73/38

* cited by examiner

*Primary Examiner* — Son T Le
*Assistant Examiner* — Alex T Devito
(74) *Attorney, Agent, or Firm* — Robert A. deGroot

(57) ABSTRACT

An apparatus and method for measuring molecular diffusivity in porous powders or minerals, e.g., the microporous synthetic minerals used for gas separation and chemical catalysis, were invented that allows a varying pressure in the gas around the powder during the measurement. This obviates the need for the pressure to be constant and the attendant complicated component parts. A mass balance model equation of the sample cell with the diffusivity as an adjustable parameter is used to deduce the sample cell pressure change versus time (uptake curve) until the equilibration of gas diffusion into the powder. A numerical analysis method is used to solve the mathematical model to compute a simulated uptake curve. Curve fitting of the simulated and measured uptake curves is used to optimize the diffusivity parameter, which gives the measured diffusivity. The apparatus and method are simple, easy to use, and automation is also simple.

12 Claims, 6 Drawing Sheets

METHOD TO MEASURE A MOLECULAR DIFFUSION COEFFICIENT IN A POROUS POWDER

CROSS-REFERENCE TO RELATED APPLICATIONS

This is a division of application Ser. No. 14/530,754, filed Nov. 2, 2014. Priority is claimed pursuant to 35USC119a,b from People's Republic of China patent application number 201410515969.2, filed on Sep. 29, 2014, a certified copy of which was filed in application Ser. No. 14/530,754, filed Nov. 2, 2014.

BACKGROUND OF THE INVENTION

An aspect of this invention relates to the characterization of porous powders of geological and synthetic minerals used in industrial gas separation and solid catalyzed chemical processes wherein the speed of molecular diffusion in the porous powder is measured. In porous powders, different molecules diffuse at different speeds, that is, they have different diffusion coefficients, and the difference in the diffusion coefficients mainly determine how well they perform in the separation of gases or as catalysts. The embodiments provide a simple method and apparatus for measuring a molecular diffusion coefficient in a porous powder. The term "porous powder" is to be understood to refer to powders that comprise minerals that have porous cavities or channels and also those that comprise aggregates of nonporous minerals compressed to form porous particles. The term "diffusion coefficient" is also known as the "diffusivity".

The speed at which molecules move into and out of a porous powder, which is also known as the internal diffusion rate, can limit the reaction rate and control the selectivity when the powder is the catalyst of a reaction. Knowledge of this diffusion rate can be used to guide the manufacture of a better catalyst. In another important application, differences in the diffusion rates can be utilized to separate the components in a gas mixture. In this invention, the term "diffusion" is used in a narrower sense than in general to mean the internal diffusion of molecules inside a porous powder. Depending on the size of the pores in the powder, the molecules would diffuse as molecules in a gas phase or when the pores are so small as to be of molecular dimensions and there is no distinct gas phase, they diffuse as an adsorbed phase. The diffusion coefficient for the molecular diffusion inside a porous powder is the parameter which is used to characterize the diffusion rate. Thus, the ability to easily carry out the quantitative measurement of the diffusion coefficient is highly advantageous for the development of useful porous powders.

The techniques for the measurement of a diffusion coefficient are described in the monograph, *Diffusion in Nanoporous Materials*, by Jorg Karger, Douglas M. Ruthven, and Doros N. Theodorou (Wiley-VCH, 2012), who divided these techniques into microscopic and macroscopic techniques. The microscopic techniques are based on the random walk or Einstein description of diffusion and they use the tracing of the path of tracer molecules inside the pores to measure the diffusion coefficient. However, because these techniques must trace particular molecules, they must be capable of the detection of distinct molecules and their molecular movement, and in general, they use expensive instrumentation and sophisticated procedures, e.g., the use of pulsed field gradient nuclear magnetic resonance, quasi-elastic neutron scattering, interference microscopy or confocal fluorescence microscopy. These techniques are not suitable for an ordinary research laboratory or for industrial use.

In a common research or industrial laboratory, the use of one of the macroscopic techniques is more reasonable. These have been based on sorption kinetics and a relaxation method which is usually a step response method, where a step change from $P_0$ to $P_\infty$ is made in the gas pressure of the gas surrounding the porous powder and the curve of the concentration of the molecules in the porous powder versus time (called the soption or uptake curve) is measured as the system relaxes to its new equilibrium state. In the prior art, most experimental techniques measure the uptake curve by using a highly sensitive microbalance to measure the change in the weight of the powder versus time. However, this is disadvantageous because these microbalances are very expensive, and so there is an incentive to instead measure some changes in the gas surrounding the powder versus time as the response curve from which the uptake curve can be deduced, e.g., in the prior art, the gas replenishment rate is used, but so far there has been no easy technique for this measurement. Such a response curve is also usually known as an uptake curve, so the method is also known as the uptake curve method. The diffusion coefficient is obtained by a curve fitting method with the use of Fick's Second Law to describe the diffusion in the porous powder, namely, Eq. (1)

$$\frac{\partial q}{\partial t} = D_c \frac{\partial^2 q}{\partial x^2} \tag{1}$$

and its initial and boundary conditions $$t < 0, P = P_0, q = q_0 (\forall\, x) \tag{2a}$$

$$t \geq 0, P = P_\infty, q|_{x=R} = q_\infty, \left.\frac{\partial q}{\partial x}\right|_{x=0} = 0 \tag{2b}$$

$$q_0 = f(P_0), q_\infty = f(P_\infty) \tag{2c}$$

In Eqs. 1 and 2, P is the pressure, q is the molecular concentration inside the porous powder particle, t is the time variable, x is the space variable, $D_c$ is the diffusion coefficient parameter, the subscript 0 denotes initial condition, the subscript $\infty$ denotes the new equilibrium condition, R is the length of the diffusion pathway in the particle, and q=f(P) denotes the functional form of the equilibrium relationship between the concentration inside the particle and the gas pressure, which is also known as the adsorption isotherm. Briefly, Eqs. 1 and 2 are used with an assumed value of the diffusion coefficient parameter to compute a simulated uptake curve which is compared with the experimental uptake curve. The value of the diffusion coefficient parameter in Eq. (1) is then changed to optimize the fit between the simulated and experimental uptake curves, with its value at the best fit being used as the measured diffusion coefficient.

In the prior art, the methods and apparatuses use an analytical solution of Eqs. 1 and 2 to compute the simulated uptake curve. Since an analytical solution is only available when the boundary condition which comprises the pressure of the gas environment surrounding the particle is a constant pressure, namely, Eq. 2b, therefore, the measurement has to be made with a constant pressure of gas. That is, in these methods and apparatuses, the gas environment of the particle has to be held at a constant pressure. Thus, when a step response method is used, the change in the gas environment was a very rapid change from one constant pressure to another constant pressure. In most of the prior art, the second pressure is maintained constant by using a very large volume of gas environment surrounding the powder so that the amount of gas that diffuse into the powder is a negligible fraction of it. However, this means that an auxiliary means must be used to measure the amount of gas that has diffused into the powder, and most apparatuses use a highly sensitive microbalance, which has the disadvantage that such a microbalance is very expensive and even then still does not have the very high sensitivity desired. An example of this type of apparatus was described in a paper by Youngquist, Allen and Eisenberg (*Industrial and Engineering Chemistry, Product Design Development,* 10 (1971) 308). Another problem that the apparatus of this type faces is that its use of a large static volume of gas that surround the powder sample gives rise to the question of whether the gas pressure is homogeneous. An apparatus to solve this latter problem made use of a new type of microbalance that can be used in a gas flow. This apparatus which used a flowing gas system and a tapered element oscillating microbalance (TEOM) was described in a paper by Zhu, Kapteijn and Moulijn (*Microporous and Mesoporous Materials,* 47 (2001) 157-171). However, the TEOM is a much more expensive microbalance and it is not suitable for use in a common laboratory or industrial laboratory.

Due to the disadvantage that available commercial microbalances are very expensive and yet still cannot give a really satisfactory sensitivity and resolution, there is an incentive to develop a technique to measure some change in the gas phase surrounding the powder as the response curve instead of measuring the weight of the gas added into the powder. An example of this approach is the method and apparatus in U.S. Pat. No. 4,762,010 to Borghard and Schoennagel, which used a flow controller that was capable of feeding in gas at very slow flow rates to replenish or make up for the gas that has diffused into the powder in order to keep the gas pressure constant. They used the measurement of the flow rate of the make-up gas to deduce the amount of gas that has diffused into the powder versus time or the uptake curve. This patent teaches that it is necessary to have gas feed rates that are very, very slow during the measurement because the amount of gas diffusing into the powder is very small. It is evident that this need leads to many problems, such as (1) the need to have additional complicated component parts and procedures to control the very, very slow replenishment flow rate needed to maintain a constant pressure around the powder, (2) a very slow flow rate has to be measured, which was measured by a pressure change, but the corresponding pressure change was extremely small, which made the control of the flow rate very difficult and resulted in poor accuracy, and (3) in order to make the pressure change larger, the container that supplied the feed gas was made to be very small, but because it was very small, its supply of feed gas was limited and the measurement can only be made for a very small range of pressure. Thus, the apparatus has not been much used.

U.S. Pat. No. 6,981,426 to Wang, Wei and Wang teaches a method that use fewer additional complicated component parts, but this was achieved at the expense of doing away with the automatic control of the required very slow replenishing gas flow rate. However, because there was no automatic control of the gas flow rate, the measurement procedure was made more complicated and tedious because a manual control of the gas flow rate had to be used, which is very inconvenient and labor intensive.

As discussed above, a basic difficulty that the prior art methods have to face is the control of the required very slow replenishment or make-up gas flow rate needed to maintain a constant pressure in the gas surrounding the powder sample. To avoid this difficulty, the more recent developments in the measurement of internal diffusion coefficients have turned to using apparatuses and methods that use a constant partial pressure of the measurement gas, instead of a constant total pressure, in the gas phase surrounding the powder sample so that the concentration change can be used to deduce the uptake curve. This is usually achieved with the use of a flow system and the use of a constant ratio of flow rates of the gases. However, gas flow controllers can only be reliably used for gas flow rates above 10 $cm^3$ per minute. This together with that it is desirable to carry out a diffusion measurement in the linear adsorption isotherm regime, which requires the partial pressure of the measurement gas to be low and so its mole fraction in the gas phase should be only a few percent, requires that the total gas flow rate should be a few hundred $cm^3$ per minute. This is a high flow rate for a laboratory apparatus, and it leads to the problem of the production of turbulence whenever there is a change in the flow rate of a component gas, such that it is not possible to produce a sharp change in the gas mole fractions of the composition gases. This turbulence means that the gas phase composition is highly erratic and its measurement is quite unreliable for some time after the step change had been made, which includes the period with much of the significant data for calculating the diffusion coefficient. One way of trying to solve this is to use the detection of the weight change in the adsorbed phase, as was done in the work cited above by Zhu, Kapteijn and Moulijn who used a flow system and a TEOM. However, as pointed out above, the TEOM is a very expensive microbalance and not suitable for common use. Another way of solving this is to use only the data collected a long time after the step change had been made, which was invented and reported in a paper by Eic and Ruthven (M. Eic, D. M. Ruthven; *Zeolites,* 8 (1988) 40-45) and now known as the long time limit zero length column (ZLC) method. However, this solution is unsatisfactory because it has to assume that the powder sample is completely homogeneous, that is, the long time limit data gives the same diffusion coefficient as the short time limit data, which is unlikely with most practical samples. The ZLC method has also been developed to use the complete data set but the technique is difficult and it needs special instruction by the inventors to be able to collect the data at short times after the step change, which is highly disadvantageous for common use.

Yet another way of trying to solve the problem of the turbulence that exist after a change in gas flow rate is to use some experimental parameters to characterize its effects and then use these parameters to subtract the effects of the turbulence, which was reported in a work by Guo and coworkers (Juhua Guo, Yuxin Li, Yanghuan Huang, Dezheng Wang; *Journal of Nanoscience and Nanotechnology,* 14(9) (2014) 6858-6864). Although their apparatus is simple and is basically that used in the chromatographic method, the preliminary work needed to characterize the turbulence is very time consuming, and hence disadvantageous. The chromatographic method, on which this work by Guo and coworkers was based, is basically a long time limit method, which can only be used with highly homogeneous sample powders.

Other methods have also been devised to solve the shortcomings discussed above, which include the frequency response method, which has been described in a work by Yasuda and Yamamoto (Y. Yasuda, A. Yamamoto; *Journal of Catalysis*, 93(1) (1985) 176-181) and the temporal analysis of products (TAP) method, which has been described in a work by Keipert and Baerns (O. P. Keipert, M. Baerns, *Chemical Engineering Science*, 53(20) (1998) 3623-3634). However, none of the methods has received much common use, and there is still a need for a simple and convenient method to measure the diffusion coefficient. The present invention meets this need. It is based on the discovery that in order to measure the diffusion coefficient in a porous powder, there is no need to make a sharp change in the gas phase environment of the powder sample, and that a gradual change can be equally well used. This resulted in a means to measure the molecular diffusion coefficient in a porous powder that used only the simple apparatus and procedure used to make a gas adsorption measurement. The measurement technique used in this invention is part of the art generally referred to as "physical modeling" in which the diffusion coefficient is measured by the optimization of the diffusion coefficient parameter in the physical model where the criterion used in the optimization is the best fit between the uptake curve calculated by the physical model and the experimentally measured uptake curve.

BRIEF SUMMARY OF THE INVENTION

In accordance with one aspect of this invention, a method for measuring a molecular diffusion coefficient in a porous powder comprise:
(a) providing a gas flow control means in communication by conduit with a supply container at an inlet to said gas flow control means and in communication by conduit with a sample cell with a weighed amount of the porous powder at an outlet to said gas flow control means, further providing the supply container is of known volume in contact with a supply container temperature measuring means and in communication by conduit: with a supply container pressure measuring means, by valving with at least one gas supply, and by valving with a vacuum pump assembly, and further providing the sample cell is of known volume in contact with a sample cell temperature measuring means at a conduit to the sample cell and in communication by conduit: with a sample cell pressure measuring means and by valving with a vacuum pump assembly;
(b) determining a curve of sample cell pressure versus time further comprising treating the porous powder into a known chemical state, keeping the constant temperature bath at a fixed temperature, evacuating by vacuum pump assembly the supply container and sample cell and then isolating the supply container and sample cell, and supplying a gas to the supply container, then using the gas flow control means to allow communication between the supply container and the sample cell for a period between one to thirty seconds, and measuring the pressure and temperature in the supply container and the pressure and temperature in the sample cell as a function of time;
(c) calculating a curve of sample cell pressure versus time to fit the curve obtained in step (b) further comprising using numerical analysis means to provide a computer program comprising a mass balance equation of the sample cell with the diffusion coefficient as a parameter, and using a computer with the computer program and an estimated value of the diffusion coefficient and the measured pressure, temperature and volume of the supply container and measured volume, temperature and weight of powder in the sample cell to calculate said curve of sample cell pressure versus time;
(d) repeating the computation in step (c) thereby to optimize the diffusion coefficient parameter by finding the best fit between the computed curve of sample cell pressure versus time and the corresponding curve measured in step (b), and using the optimized diffusion coefficient as the measured diffusion coefficient.

Accordingly, some advantages are that the measurement is simpler and more accurate because, as distinct from prior art, there is no need to maintain a constant pressure in the gas surrounding the powder during the measurements. The method and apparatus are simpler because the pressure in the gas surrounding the powder is allow to decrease naturally, as would happen when some gas diffuse into the powder, rather than using some artificial means to force it to be roughly constant. The experimental results have a higher accuracy because of the use of a reliably measured pressure change in the gas surrounding the powder instead of a poorly controlled pressure that is roughly constant.

Figure 1:
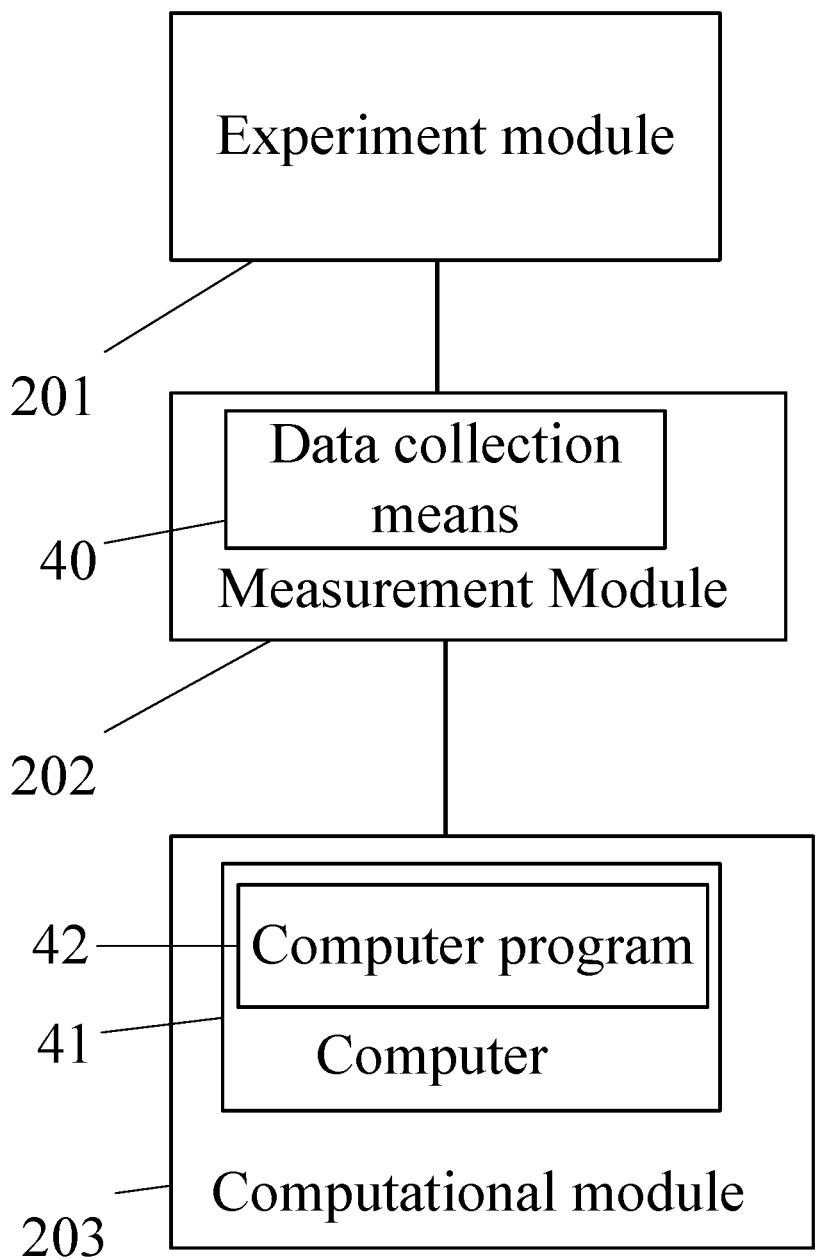
FIG. 1 is a general schematic showing the modules of an apparatus used to measure the molecular diffusion coefficient inside a porous powder.

In the drawings, the reference numerals are:
10—gas flow control means; 11—sample cell; 12—porous powder sample; 13—supply container; 14—reference chamber; 16—gas supply; 17—gas supply; 20—constant temperature bath; 21—sample cell pressure measuring means; 22—supply container pressure measuring means; 23—supply container pressure difference measuring means;
25—reference chamber temperature measuring means; 26—supply container temperature measuring means; 27—sample cell temperature measuring means; 31—vacuum pump assembly; 32—valve; 33—valve; 34—valve; 35—valve; 36—valve; 37—valve; 40—data collection means; 41—computer; 42—computer program; 201—experiment module; 202—measurement module; 203—computation module.

DETAILED DESCRIPTION OF THE INVENTION—FIRST EMBODIMENT

This embodiment measures the molecular diffusion coefficient inside a porous powder by supplying the molecules as a gas stream fed in for a short time into a sample cell containing the powder. It is novel in providing for that the gas stream is fed in for only a short time but the feed is also not sudden and does not comprise a sharp opening and closing of the gas flow control means. Although the opening and closing of the gas flow control means is for a quite short time, they should be steady to avoid any surge in pressure in the sample cell. After an initial pressure increase due to the short time when there was a supply of gas, the pressure of the gas surrounding the porous powder is then allowed to decrease naturally due to gas diffusion into the porous powder until equilibration is reached, that is, there is no further change in the sample cell pressure. Its novel feature is in the provisions made to obviate the need to maintain a constant pressure in the sample cell. The principle of the measurement will be first described, then the apparatus, and finally the way to make a measurement.

The principle of the measurement is based on the art referred to as "mathematical modeling" or "physical modeling". A mathematical model that includes the diffusion process is constructed which contains the diffusion coefficient as a parameter, wherein the model is further designed so that when it is given a value for this parameter, it can calculate a simulated uptake curve. The technique used to deduce the diffusion coefficient is popularly known as "curve fitting", which is basically an optimization procedure where the value of the diffusion coefficient parameter in the physical model is adjusted to give the best fit between the uptake curve calculated by the physical model and the experimentally measured uptake curve. This is also the principle used in the prior art in which the model used is Eqs. 1 and 2 presented above. An important aspect of the discussion above is that the use of the model of Eqs. 1 and 2 brings with it the very difficult problem of the need to keep a constant pressure or partial pressure of the measurement gas, which is because Eq. 2b comprises the condition that the porous powder has a constant pressure or partial pressure of the measurement gas in its gas environment. The present invention is based on the discovery that with an auxiliary equation of a mass balance in the sample cell, the mathematical model of the diffusion process in the porous powder does not need to have a constant pressure or partial pressure of the measurement gas in its gas environment. Thus, in the measurement of the diffusion coefficient in a porous powder, there is then no need to make a sharp change in the pressure of the gas around the powder sample, and a gradual change in the pressure can be used. This results in a means to measure the molecular diffusion coefficient in a porous powder that needs to use only the simple apparatus and procedure for a gas adsorption measurement with the addition of a mathematical model and curve fitting procedure.

Figure 2:
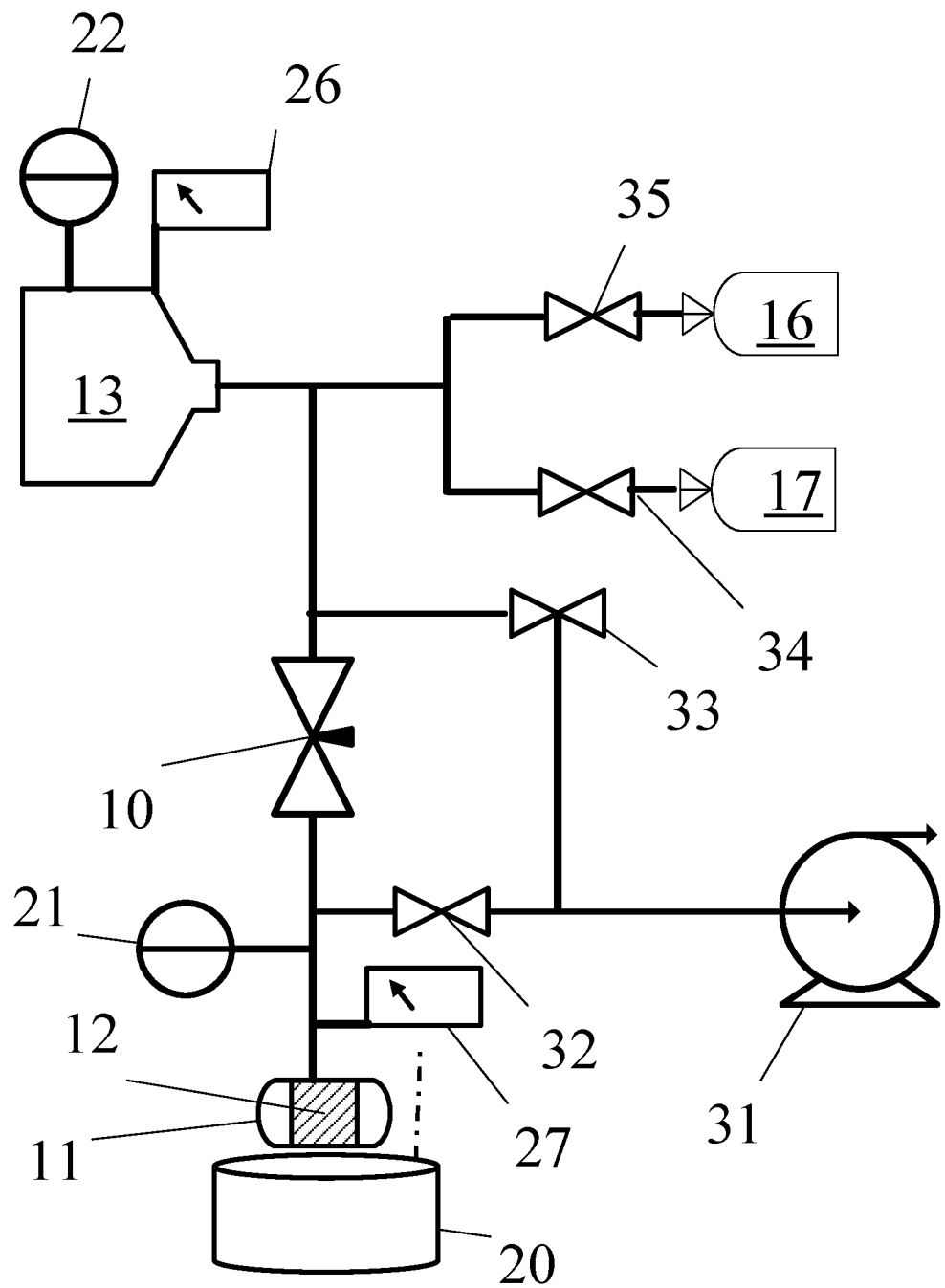
FIG. 2 is a detailed schematic view of a first embodiment.

The apparatus and method to measures the molecular diffusion coefficient inside a porous powder is now described. The apparatus comprises the three modules shown in FIG. 1, namely, an experiment module 201, a measurement module 202 and a computational module 203. The components of the experiment module and measurement module are shown in FIG. 2. The experiment module comprises supply container 13, sample cell 11 and porous powder sample 12, gas flow control means 10, constant temperature bath 20, vacuum pump assembly 31, and gas supplies 16 and 17. The measurement module comprises sample cell pressure measuring means 21 and supply container pressure measuring means 22, supply container temperature measuring means 26 and sample cell temperature measuring means 27, and data collection means 40. The computational module comprises a computer 41 and computer program 42. The experiment module is used to prepare the system for a measurement, and comprises first evacuating and then filling supply container 13 with the measurement gas, evacuating sample cell 11, and then opening gas flow control means 10 for a brief period to allow a transient flow of gas from the supply container into the sample cell to initiate a measurement. The measurement module is used to measure the pressure decrease and temperature in the supply container until the gas flow is stopped and the pressure and temperature in the sample cell as a function of time until equilibration is reached. The computational module is used to apply an optimization technique to get the diffusion coefficient by seeking the best fit between the calculated and measured sample cell pressure versus time (uptake) curves. Data collection means 40 is an analog to digital (A/D) conversion board placed in computer 41. It receives data signals from the sensors of sample cell pressure measuring means 21 and supply container pressure measuring means 22 and supply container temperature measuring means 26 and sample cell temperature measuring means 27, which are converted into digital data that are saved in computer 41. The data collection means can also be a person who reads the meter readings of the sensors and then records these readings into the computer. This embodiment uses MKS Baratron Model 120AA capacitance manometers as the pressure measuring means in order to have a higher measurement precision. This model has a measurement precision which is less than 0.3% of the reading shown by the measuring means. Other types of manometers or multiple manometers with different ranges can also be used. After data collection, computational means 203 is used to deduce the measured diffusion coefficient by a curve fitting techniques using the calculated and measured uptake curves.

The measurement proceeds as follows. A weighed amount of about 0.1 g of porous powder sample 12 is placed in sample cell 11. The sample has to be first treated to get it into a known chemical state, e.g., a degassed and dehydrated state for a zeolite, before the measurement, which is called a pretreatment, but before performing this pretreatment, the volume of the sample cell is measured using the expanded pressure that results from the supply of a known amount of helium gas. This volume measurement is described in textbooks on gas adsorption and so this will not be discussed here. The volume of the sample cell can alternatively be measured after the diffusion coefficient measurement. Sample cell 11 is connected to gas flow control means 10 at its outlet by a tubing and the volume of the sample cell should be understood to include the volume of all the tubings, e.g., in FIG. 3, this volume would include the volumes inside the pieces of tubing to gas flow control means 10, valve 32 and sample cell pressure measuring means 21 and the volumes inside these components. In many measurements, powder sample 12 is placed in a constant temperature bath at a different temperature from room temperature, and in these cases, the gas volume should include the effect of the temperature and if the gas is non-ideal at this temperature, a correction should be made for this. For some samples where the pretreatment requires a flowing gas, the sample cell should be modified to allow a gas flow (not shown in FIG. 2). The pretreatment procedure depends on the nature of the sample and can differ widely, but would be well known to someone skilled in the art and so this will not be discussed here. For example, with a catalyst sample, the aim of the pretreatment would be to get the sample into a catalytically active state. For the pretreatment, the part of the sample cell that contains the powder sample is placed in constant temperature bath 20, which can be a liquid constant temperature bath or an electrical furnace controlled to be at a constant temperature. After the pretreatment, with gas flow control means 10 shut, vacuum pump assembly 31 is used to evacuate the sample cell and sample through valve 32 and constant temperature bath 20 is set to the measurement temperature. At the same time, the vacuum pump assembly is also used to evacuate supply container 13 through valve 33. The vacuum pump assembly is a turbo-molecular pump and mechanical pump combination, but other pump combinations for gas evacuation can also be used.

The other inlet arm of gas flow control means 10 is connected by tubing to supply container 13, which is being prepared to be used to supply the measurement gas. The volume of the supply container would have been measured and so it is a known quantity; otherwise it has to be measured after the diffusion coefficient measurement. This volume should be understood to include the volume of the tubings, e.g., in FIG. 2, this volume would include the volumes inside the pieces of tubing to gas flow control means 10, valves 33, 34, and 35, and supply container pressure measuring means 22 and the volumes inside these components. Pump assembly 31 is used to evacuate supply container 13 through valve 31. If a previous measurement had used the same gas and the gas in the supply container is still pure, the evacuation can be omitted. After evacuation, gas supply 16 and valve 35 or gas supply 17 and valve 34 is used to fill supply container 13 with the measurement gas to a chosen pressure, which is chosen by experience to have enough gas to complete a series of measurements. The gas supply can be a high pressure gas cylinder with a low-pressure pressure controller and gauge or a glass tube filled with a liquid kept at a constant temperature for gases that are liquid at room temperature and atmospheric pressure. More gas supplies can be added to the apparatus if it makes the apparatus more convenient to use.

After the supply container has been filled with the gas and the sample is at the measurement temperature and the sample cell has been evacuated, valve 32 is shut to isolate the sample cell. Then gas flow control means 10 is opened briefly to supply a controlled amount of the gas to the sample cell. Gas flow control means 10 is a fine control leak valve which is manually controlled. This is the type of leak valve that is used to dose very small amounts of a gas into a vacuum system and can be bought from suppliers of vacuum parts. Other types of flow control valves, such as a manual needle valve or a computer controlled solenoid valve or servomotor valve, can also be used. The gas flow control means is used to control the amount of gas supplied to the sample cell so that there is only a small pressure increase. The amount of gas supplied is determined by the nature of the experiment and experience of the operator. In our measurements, the amount is chosen to allow 10 to 20 doses of the gas to be made during the overall pressure increase in the sample cell from vacuum to the adsorption saturation pressure of the supplied gas. These would give data collected at 10 to 20 different pressure ranges, from which the values of the diffusion coefficient can be obtained for different pressure or adsorbate concentration. Although gas flow control means 10 is to be opened or kept in its communicate state for only a brief period, which is from 1 to 30 seconds, the valve is to be open in a steady manner, which is not to be a very sudden open and shut process that takes less than one second.

After gas flow control means 10 is opened, the pressure in supply container 13 decreases. The pressure decrease is measured by subtracting the pressure measured by supply container pressure measuring means 22 at any time t from the pressure measured before gas flow control means 10 was opened. This pressure decrease is recorded by data collection means 40 as a function of time until after gas flow control means 10 is shut. After gas flow control means 10 is opened, the pressure in sample cell 11 first increases, and then after the gas flow control means is shut, the pressure decreases due to diffusion into powder sample 12. The pressure is measured by sample cell pressure measuring means 21 and recorded by data collection means 40 as a function of time until the pressure does not change, that is, until equilibration was reached. The recorded data of sample cell pressure versus time comprise the uptake curve, which is used for curve fitting to deduce the diffusion coefficient. Due to that the pressure is affected by the temperature, supply container temperature measuring means 26 and sample cell temperature measuring means 27 are used to measure, respectively, the temperatures of supply container 13 and the tubing leading to sample cell 11 so that the effect of any temperature change can be accounted for. This completes one cycle of data collection which can be used to determine the diffusion coefficient in this range of adsorbate concentration. The adsorbate concentration is the amount of molecules in the porous powder per gram of powder. After the sample cell pressure does not change any more, the measurement can be repeated to determine the diffusion coefficient in another range of adsorbate concentration, which can be used to see if it changes with the adsorbate concentration. If the pressure in the supply chamber is sufficiently higher than the pressure in the sample cell, there is no need to refill the supply chamber for this. The measurements can be repeated until the pressure in the sample cell has reached a pressure beyond which no additional gas uptake occurs in the porous powder, which is its saturation pressure. In addition to the diffusion coefficient, those skilled in the art would also see that these data comprise the data of adsorbed amount versus pressure, which is the adsorption isotherm. These data can be curve fitted to determine the parameters in the adsorption isotherm, which is an equation that expresses the thermodynamic equilibrium relationship between the gas pressure and adsorbate concentration. This adsorption isotherm can then be used in Eqs. 14b and 14c (see below) of the mathematical model used to determine the diffusion coefficient.

Computational module 203 is used with an initial estimate of the diffusion coefficient parameter in Eq. 13 (see below) together with the measured pressure decrease and temperature and known volume of the supply container and measured volume, temperature and mass of powder in the sample cell to calculate a curve of sample cell pressure versus time (uptake curve). Then the value of the diffusion coefficient parameter is changed in order to optimize the fit between the computed uptake curve and the measured uptake curve. The optimized diffusion coefficient parameter that gives the best fit is taken to be the measured diffusion coefficient.

From the description above, it can be seen that after the opening of gas flow control means 10, there is no adding of make-up gas into sample cell 11. This is different from the prior art method, that is, the method of this invention avoids the difficult supplying of a very slow continuous flow of make-up gas and instead it just needs the gas flow control means to be open for a brief period, which makes the method and apparatus simpler and more practical. This is because the mathematical model is formulated to allow the use of a variable pressure in the boundary condition that expresses the adsorption equilibrium between the gas pressure and adsorbate concentration at the surface of the porous powder, which is the adsorption isotherm (see Eqs. 14b and 14c below). In addition, in the technique in the prior art, due to the need to supply a continuous flow of make-up gas and because this gas flow is very, very small, the volume of the supply container has to be also small in order to have a measureable change in its pressure. However, when this chamber is small, although the pressure change will be large and can be reasonably measured, the pressure quickly falls to be close to that of the pressure in the sample cell and so there is a need to replenish the gas in the supply container many times. Due to that an error is introduced each time a replenishment occurs, the overall accuracy will be adversely affected. In contrast, in the present invention, the supply container can be quite large and it contains enough gas to complete the whole series of measurements, and therefore, the accuracy is better.

DETAILED DESCRIPTION OF A SECOND EMBODIMENT

Figure 3:
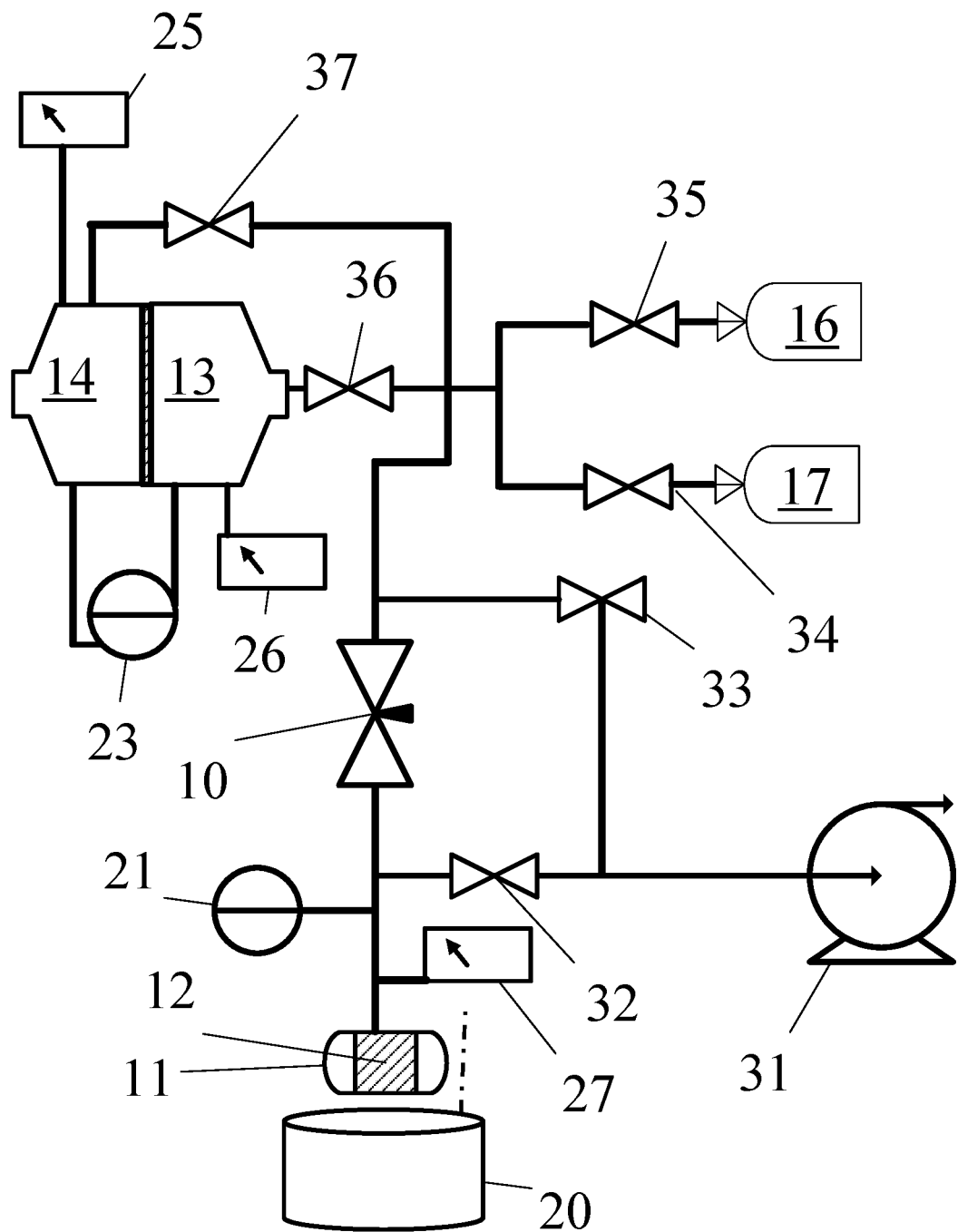
FIG. 3 is a detailed schematic view of a second embodiment.

FIG. 3 shows the schematic of a second embodiment of the apparatus. The difference between this and the first embodiment is that the pressure decrease in supply container 13 is measured with supply container pressure difference measuring means 23, which has its low pressure part connected to the supply container and the high pressure part connected to reference chamber 14. Reference chamber 14 is filled with a gas to the same or a higher pressure than the pressure in the supply container and then kept isolated so that its pressure does not change. When gas flow control means 10 is opened briefly, some gas flows out from supply container and its pressure decreases. Since there is no change in the pressure in reference chamber 14, the pressure difference recorded with supply container pressure difference measuring means 23 at any time t minus the pressure difference measured before gas flow control means 10 was opened is the pressure decrease in the supply container at time t. This method of measuring the pressure decrease will give a much higher measurement precision when supply container pressure difference measuring means 23 has a precision which is proportional to its reading, e.g., a MKS Baratron Model 120AD differential pressure capacitance manometer, which has a measurement precision less than 0.3% of the reading shown. Other types of differential pressure manometers or multiple differential pressure manometers with different ranges can also be used.

Most of the operations performed with embodiment 2 are the same as with the first embodiment, and only operations that are different will be described. These involve how to make use of reference chamber 14. Vacuum pump assembly 31 is first used to evacuate the reference chamber at the same time as when supply container 13 is evacuated by opening valves 33, 36 and 37. Then valve 33 is shut to isolate them from the vacuum pump. With gas flow control means 10 closed, gas supply 16 and valve 35 or gas supply 17 and valve 34 is used to supply reference chamber 14 and supply container 13 with the measurement gas to a chosen pressure, which is chosen by experience to have enough gas to complete a series of measurements. Reference chamber 14 is then isolated by shutting valve 37, and supply container 13 is used to supply gas to the sample cell as in embodiment 1. The pressure difference reading from supply container pressure difference measuring means 23 is sent to data collection means 40 and recorded in computer 41. Due to that the pressure is affected by the temperature, reference chamber temperature measuring means 25 is used to measure the temperature of reference chamber 14 so that the effect of any temperature change can be accounted for. In FIG. 3, it is also shown that reference chamber 14 and supply container 13 are connected by a slab of stainless steel which allows heat transfer but not mass transfer between them, which is used to minimize any temperature difference between reference chamber 14 and supply container 13.

Example Measurement Using Embodiment 2

Figure 4:
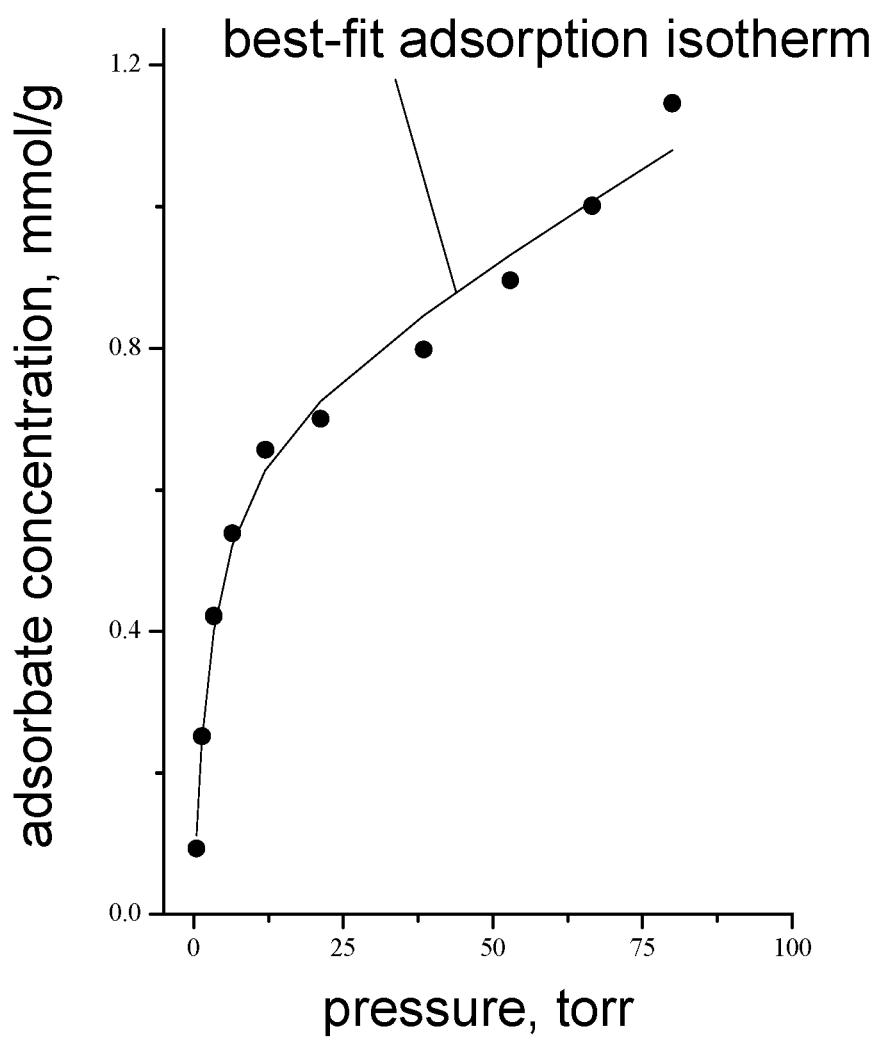
FIG. 4 shows a graph of the data of the adsorption isotherm of Example 1.

The measurement of the diffusion coefficient is now described with an example. This example measured the diffusion coefficient of propane inside a SAPO-34 zeolite sample. First, the free volume in sample cell 11, which is the volume in the sample cell not occupied by the sample, is determined. It is presumed that the volume of the supply container is already known. During a series of measurement of the diffusion coefficient with different sample cell pressures, the adsorption isotherm, which is the equation expressing the equilibrium relationship dependence of the adsorbate concentration on the pressure, can also be measured. If the adsorption isotherm is already available from a paper in the literature, this can be used instead. These measurements are described in textbooks on gas adsorption and so their details will not be described here. FIG. 4 shows the adsorbate or adsorbed phase concentration versus pressure data and the best-fit curve of the adsorption isotherm, which was the equation $$q = q_{sat}^1 \frac{b_1 P}{1 + b_1 P} + K_1 P \tag{3}$$

where q, $q_{sat}^1$, $b_1$, $K_1$, and P are the adsorbate concentration, acid site concentration of the sample, adsorption equilibrium constant on the acid sites, adsorption equilibrium constant on the nonacid sites and gas phase pressure in the sample cell, respectively. The fitted values of the parameters were: $q_{sat}^1$=0.70 mmol/g, $b_1$=0.36 l/Pa, and $K_1$=0.0051 mmol/g/Pa. q and P have units of mmol/g and Pa. Eq. 3 is one example of an adsorption isotherm, which is an equation expressing the thermodynamic equilibrium adsorbate concentration on the outer surface of a powder particle as a function of the sample cell pressure. Other gases adsorbed on other porous powder can have different adsorption isotherm equations to describe the equilibrium relationship between the gas and adsorbed phases. Eq. 3 is used in Eqs. 14b and 14c (below), which comprise the boundary condition for Eq. 10. Alternatively, if an adsorption isotherm equation is already known from the literature, this can be used or if the adsorption data are too sparse to allow a curve fitting procedure, the parameters in the adsorption isotherm equation would need to be treated as additional parameters to be fitted for during the curve fitting to get the diffusion coefficient.

Figure 5:
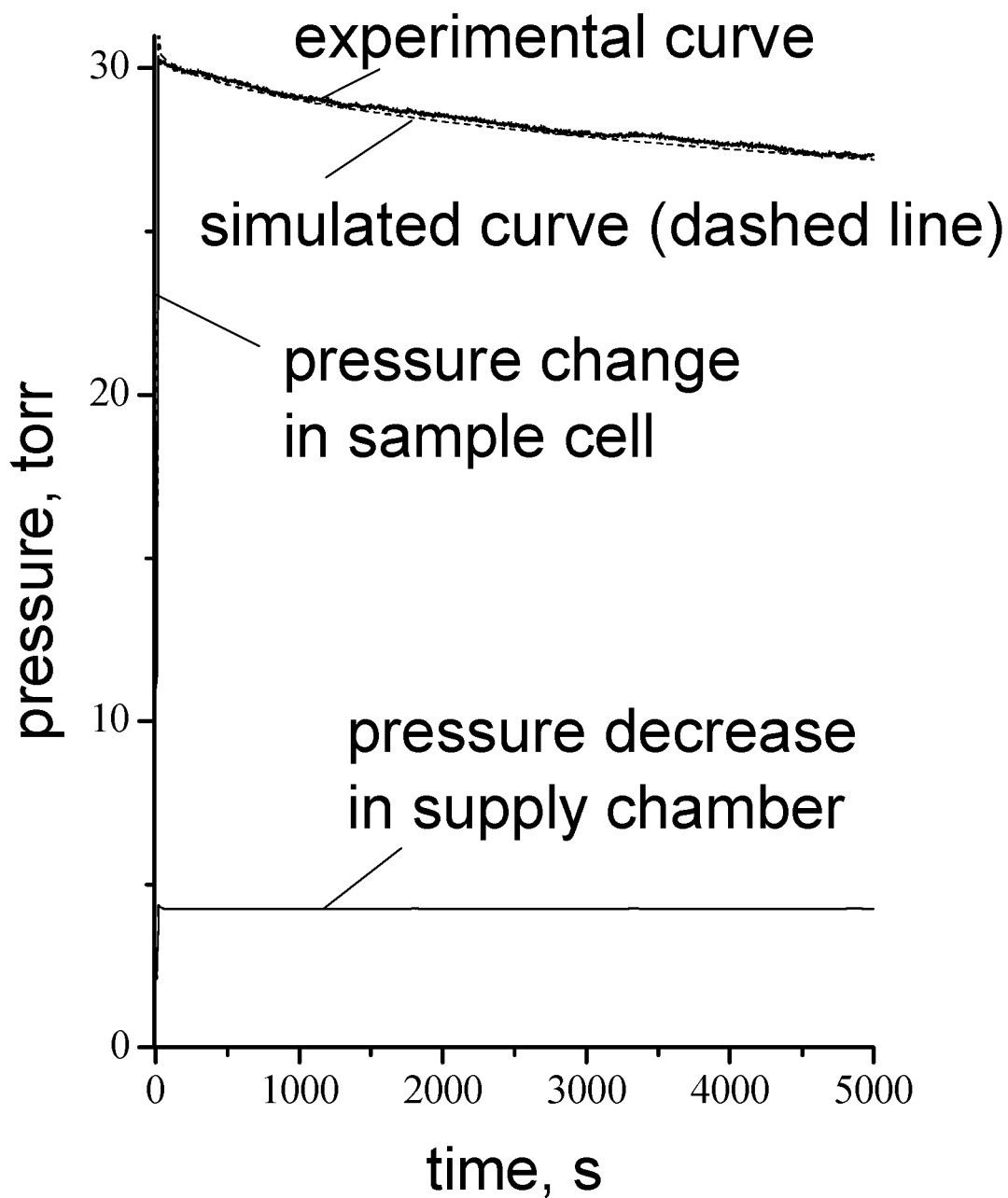
FIG. 5 shows graphs of the data used to calculate the molecular diffusion coefficient of Example 1.

Many cycles of measurement can be made where in each cycle a curve of the sample cell pressure versus time (uptake curve) is used for curve fitting to determine the diffusion coefficient in a particular range of pressure. In this example, FIG. 5 shows the data for when the sample cell pressure is about 30 torr. The following symbols and values are used:

V1 is the volume of supply container 13, V1=648.5 cc (previously measured);

T1 is the temperature of supply container 13, T1=29.0° C. (did not change with time during the measurement);

T2 is the temperature of the part of sample cell 11 that is not in the constant temperature bath, T2=29.0° C. (did not change with time during the measurement);

Vu is the volume of the part of sample cell 11 at room temperature, Vu=10.35 cc;

Vc is the volume of the part of sample cell 11 in the constant temperature bath, Vc=62.2 cc;

T3 is the temperature of the constant temperature bath, T3=29.0° C. (did not change with time during the measurement);

dP is the pressure difference between reference chamber 14 and supply container 13 (changes with time during the measurement);

P is the pressure in sample cell 11 (changes with time during the measurement);

N is the number of moles of gas in the gas phase in sample cell 11 (changes with time during the measurement);

$m_{cat}$ is the weight of the porous powder sample in sample cell 11, $m_{cat}$=0.10 g;

F is the molar flow rate of the gas into sample cell 11 (changes with time during the measurement).

FIG. 5 shows an example of the data collected when gas flow control means 10 was open for a brief period of about 13 seconds to give a transient flow of gas into sample cell 11. It can be seen from the upper curve that there is first an increase in the sample cell pressure due to the gas fed into it, and then after the gas feed was shut off, there is a gradual decrease as gas diffuse into the porous powder sample. During the measurement, the sample cell pressure changed, which distinguishes this invention from the methods in the prior art. The significance of this is that it is advantageous because this is how the natural process occurs, and there is no need to add complicated component parts and procedures to prevent the natural pressure decrease as the gas diffuse into the powder. In addition, in order to have the best accuracy possible, provisions were made to measure the pressure in sample cell 11 and pressure decrease in supply container 13 with high precision means that have measurement precision that were less than 0.3% of the reading. A further consideration is that the volumes of sample cell 11 and supply container 13 have to be chosen well. For 0.1 g of a porous powder sample with a specific surface area of 300 m$^2$/g, the volumes of sample cell 11 and supply container 13 can be chosen to be about 70 and 650 cm$^3$, respectively. FIG. 5 shows that after the brief flow of gas from the supply container to the sample cell, the pressure decrease in the supply container was 2.5 torr. That is, supply container pressure difference measuring means 23 showed a pressure difference of 2.5 torr. Since the precision is 0.3% of the reading, the measurement error was 0.003×2.5=±0.0075 torr, which showed that the pressure difference was quite precisely measured. Furthermore, 20 doses of gas where each dose gave about 2.5 torr pressure decrease would give a total pressure drop of about 50 torr. If the supply container was originally filled to a pressure of 900 torr, it would still have 850 torr left, which is sufficient to supply gas to the sample cell until atmospheric pressure. Usually, it is convenient to have a supply container with a gas amount sufficient to increase the pressure in the sample cell to a pressure beyond which no additional gas uptake occurs in the porous powder. From FIG. 5, it is seen that the sample cell pressure decreased by about 4 torr after gas flow control means 40 was shut, which was due to diffusion into the sample. The pressure in the sample cell during this process was about 30 torr, and since the precision is 0.3% of this, the measurement error was ±0.09 torr, thus the pressure decrease of 4 torr could be measured quite precisely. However, if the pressure in the sample cell during this process had been about 500 torr, the measurement error would be ±1.5 torr, which would be quite large compared to a pressure decrease of 4 torr. If this is a pressure range that is of interest, a smaller volume sample cell should be used so that the pressure decrease due to diffusion into the sample can be larger. In summary, the volumes of sample cell 11 and supply container 13 should be chosen according to the measurement needs and operator experience. From the data above, recommended volumes are between 200 and 500 cc for the supply container and between 1 and 100 cc for the sample cell, with the smaller volume giving better accuracy and the larger volume giving more convenience. Similarly, the brief period when the gas flow control means is open can be recommended to be between 1 and 30 second, with the shorter time giving more data points and the longer time giving more easily measurable pressure changes.

The procedure to get the diffusion coefficient is as follows. A mathematical model of mass balance in the sample cell is set up that contains the diffusion coefficient as an adjustable parameter. Numerical analysis is used to write the equations of the model into a form that is suitable for use in a computer program, and which a computer can run to calculate a simulated uptake curve. The diffusion coefficient parameter is optimized to get the best fit between the simulated and measured uptake curves. The mass balance equation for the sample cell is $$\frac{dN}{dt} = -x \cdot m_{cat} + F \tag{4}$$

In Eq. 4, t is the time variable, x is the molar flux per gram sample of gas diffusing into the powder sample, which is a function of time, that is, it is x(t), and F is the molar flow of gas into the sample cell, which is also a function of time, that is, it is F(t). x(t) is calculated from Eq. 15 (below). This model, that is, Eq. 4, is an equation that describes the mass balance in the sample cell as that the accumulation of moles of gas is equal to the loss due to diffusion into the powder and the gain due to flow into the sample cell.

In order to have a wide use, from the consideration that under many conditions, x(t) does not have an analytic formula but is only calculable in tabular form as values of x at different values of t, it is preferable to solve Eq. 4 by numerical analysis. The term "numerical analysis" should be understood to mean that Eq. 4 is expressed as a discretized formula in place of the differential equation, which can be by finite difference means, finite element means, finite volume means or spectral method means. One particular way to discretize Eq. 4 is by the Euler method, which is a first order finite difference method, which gives $$\frac{N_i - N_{i-1}}{\Delta t} = -x_{i-1} \cdot m_{cat} + F_{i-1} \tag{5}$$

In Eq. 5, the subscript i denotes the time index of the discretized time variable t. $\Delta t$ is the time step size, which has to be small enough for Eq. 5 to be an accurate approximation of Eq. 4. In the calculations in this example, $\Delta t$=0.1 s. Eq. 5 is solved by a time march method, namely, $$N_i = N_{i-1} - x_{i-1} \cdot m_{cat} \cdot \Delta t + F_{i-1} \cdot \Delta t \tag{6}$$

The Euler method illustrated here is an example and some other numerical analysis method can also be used.

The third term on the right hand side of Eq. 6 is calculated from the data of the pressure decrease in supply container with the use of the ideal gas law by $$F_{i-1} \cdot \Delta t = \Delta F_{i-1} = \frac{(dP_i - dP_{i-1})V_1}{RT_1} \quad (7)$$

In Eq. 7, dP is a function of t, that is, it is dP(t), and $dP_i$ is the discretized form. The times of the measured values of dP recorded in the computer did not match exactly with the discretized time steps. In this case, an interpolation technique was used to get the values at the required discretized times using the measured dP(t)~t curve. The values of x(t) or $x_i$ was obtained from the solution of the diffusion equation in the porous powder sample. The general form of this equation, which is also known as Ficks second law, is given in the monograph by Crank (J. Crank, *The Mathematics of Diffusion*, second edition, Oxford University Press, 1975) as $$\frac{\partial q}{\partial t} = div(D \ grad \ q) \quad (8)$$

which in terms of orthogonal axes is $$\frac{\partial q}{\partial t} = \frac{1}{A_\xi} \frac{\partial}{\partial \xi}\left(A_\xi D_\xi \frac{\partial q}{\partial \xi}\right) + \frac{1}{A_\eta} \frac{\partial}{\partial \eta}\left(A_\eta D_\eta \frac{\partial q}{\partial \eta}\right) + \frac{1}{A_\zeta} \frac{\partial}{\partial \zeta}\left(A_\zeta D_\zeta \frac{\partial q}{\partial \zeta}\right) \quad (9)$$

In Eq. 9, q is the adsorbate concentration or molecular concentration inside the powder particle and it is a function of t and the space variables. A and D are the cross-sectional area and diffusion coefficient, respectively, in the direction of the subscript, $\xi$, $\eta$, or $\zeta$, which denote the three generalized orthogonal space coordinates. When this equation is solved by numerical analysis, A and D can be functions of the space variables. This equation can be solved by the alternating direction implicit (ADI) method. Since the principle is the same for particles of different geometries or shapes, the method of solution to get q is illustrated below with a spherical particle.

For a spherical particle, due to the symmetry of a sphere, only the radial coordinate will have a concentration variation and Eq. 9 is simplified to $$\frac{\partial q}{\partial t} = \frac{1}{r^2} \frac{\partial}{\partial r}\left(r^2 D_r \frac{\partial q}{\partial r}\right) \quad (10)$$

In Eq. 10, r is the radial coordinate. Using the Crank-Nicolson method and j−1, j, j+1 and n, n+1 to represent discretized r and t, Eq. 10 in discretized form is $$\frac{q_j^{n+1} - q_j^n}{\Delta t} = 0.5 \frac{1}{r_j^2} \frac{r_{j+\frac{1}{2}}^2 D_{j+\frac{1}{2}}(q_{j+1}^{n+1} - q_j^{n+1}) - r_{j-\frac{1}{2}}^2 D_{j-\frac{1}{2}}(q_j^{n+1} - q_{j-1}^{n+1})}{(\Delta r)^2} + $$
$$0.5 \frac{1}{r_j^2} \frac{r_{j+\frac{1}{2}}^2 D_{j+\frac{1}{2}}(q_{j+1}^n - q_j^n) - r_{j-\frac{1}{2}}^2 D_{j-\frac{1}{2}}(q_j^n - q_{j-1}^n)}{(\Delta r)^2} \quad (11)$$

$$\text{where } D_{j+\frac{1}{2}} = \frac{1}{2}(D_{j+1} + D_j), \ r_{j+\frac{1}{2}} = \frac{1}{2}(r_{j+1} + r_j)$$

with a corresponding meaning for other subscripts with a ½ value. Eq. 10 is not defined at r=0 because of the $1/r^2$ term, and l'Hospital's rule has to be used there, which gives $$\lim_{r \to 0}\left(u_{rr} + \frac{2}{r}u_r\right) = u_{rr} + \lim_{r \to 0} \frac{2}{r}u_r = u_{rr} + 2u_{rr} = 3u_{rr} \quad (12)$$

This and the symmetry boundary condition at the center of the sphere, $$\frac{\partial q}{\partial r}\bigg|_{r=0} = 0,$$

were used to write the discretized equation at r=0 as $$\frac{q_0^{n+1} - q_0^n}{\Delta t} = 3D_0 \frac{(q_1^{n+1} - 2q_0^{n+1} + q_{-1}^{n+1})}{(\Delta r)^2} = 3D_0 \frac{2(q_1^{n+1} - q_0^{n+1})}{(\Delta r)^2} \quad (13)$$

Here, $D_0$ denotes the diffusion coefficient at r=0 (center of the sphere). Using P to denote the gas phase pressure in the sample cell, and $P_0$ and P(t) as the pressure before and after gas flow control means was opened, the initial and boundary conditions for Eq. 10 are $$t < 0, P = P_0, q = q_0(\forall \ r) \quad (14a)$$

$$t \geq 0, P = P(t), q(t)|_{r=R} = q_R^n, \frac{\partial q}{\partial r}\bigg|_{r=0} = 0 \quad (14b)$$

$$q_0 = f(P_0), q_R^n = f(P) \quad (14c)$$

In Eq. 14, R is the radius, and the subscript 0 denotes the initial conditions at t<0. At t≥0, as shown in Eq. 14b, the pressure P is a function of t, that is, P=P(t). This is the simulated uptake curve, that is, the change in the calculated sample cell pressure with time. In Eq. 14c, the equations $q_0=f(P_0)$, $q_{R^n}=f(P)$ denote the equilibrium relationship between the adsorbate concentration on the outer surface of the particle and pressure in the gas phase, which is the adsorption isotherm (equation). This was Eq. 3 in this example, but it can be some other equation in other situations. Taken together, Eqs. 14b and 14c say that at any time t (which is indicated by the discretization index n) when the pressure in the sample cell is P, the adsorption isotherm is used to calculate the adsorbate concentration on the outer surface of the particle, $q_{R^n}$. The use of the mass balance equation for the sample cell, which is Eq. 6 in this example, means that the pressure in the sample cell, P, does not have to be constant because Eq. 6 gives its value as a function of time.

Eqs. 12, 13, and 14 were solved by the Crank-Nicolson method, which is explained in the monograph by Crank cited above. This method is based on that Eqs. 12 and 13 form a tri-diagonal matrix, which can be solved with the Thomas algorithm. In this example, the step sizes used were $\Delta t=0.1$ s and $\Delta x=1\times10^{-6}$ cm (the radius of the spherical particle was $1\times10^{-4}$ cm). This method used is an example and other numerical analysis methods and step sizes can also be used. After each time step, the concentration inside the particle q is known as a function of the radial coordinate, thus the concentration gradient at the particle surface can be calculated from which x(t) is calculated using $$x(t) = \frac{4\pi R^2}{\frac{4}{3}\pi R^3} \rho D_R \frac{\partial q}{\partial r}\bigg|_{r=R} = \frac{3\rho}{R} D_R \frac{\partial q}{\partial r}\bigg|_{r=R} \quad (15)$$

In Eq. 15, ρ is the density of the porous powder sample. The use of x(t) as $x_{i-1}$ in Eq. 6 allows the value of $N_i$ to be calculated, which is converted into the sample cell pressure using Eq. 16:

$$N = \frac{PV_u}{RT_2} + \frac{PV_c}{RT_3} \quad (16)$$

In Eq. 6, $N_i$ is the discretized form of N as a function of t, that is, it is N(t) and from Eq. 16, P is obtained also a function of t, that is, it is P(t), which is the simulated uptake curve that is used for the curve fitting with the measured uptake curve.

Figure 6:
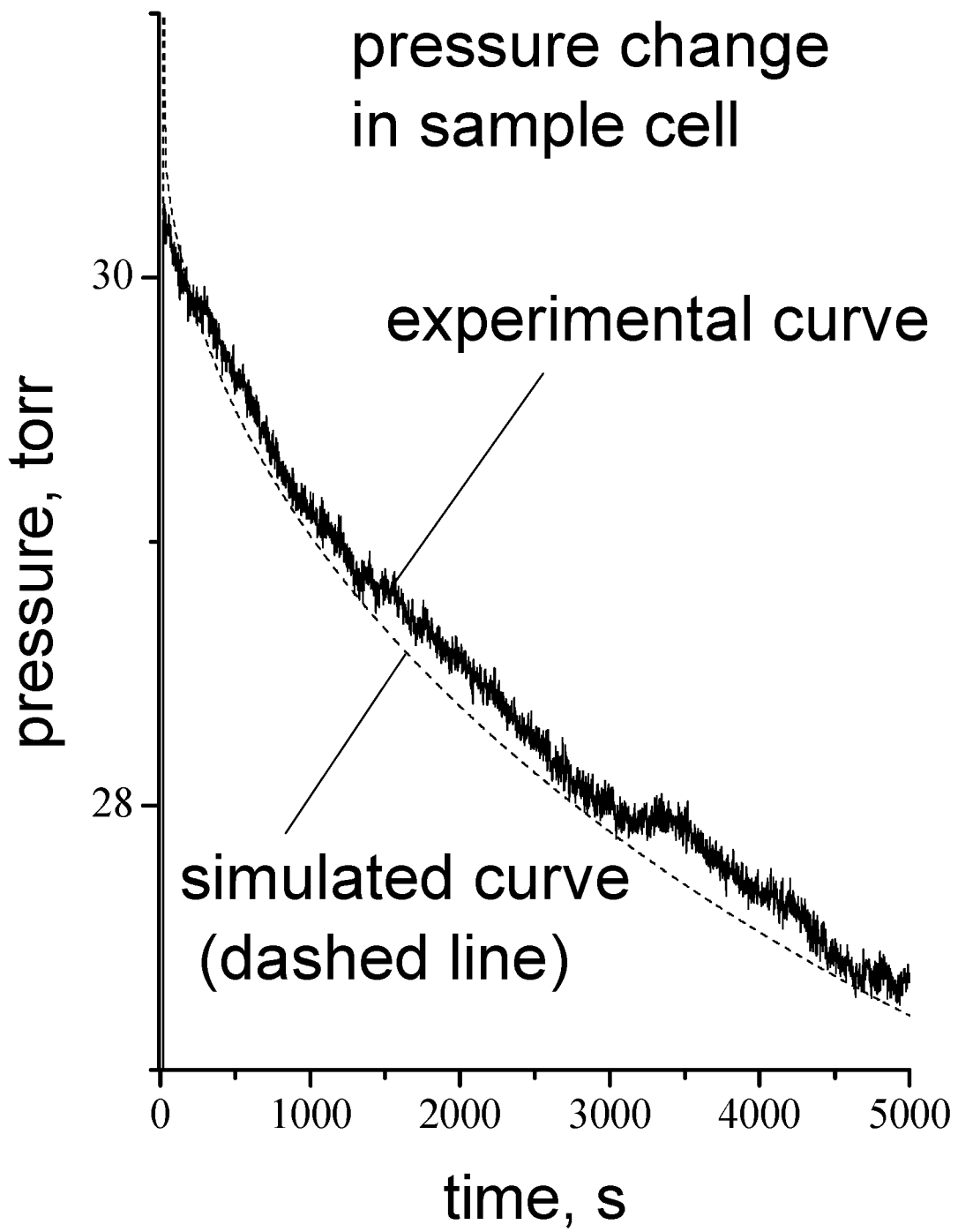
FIG. 6 shows an expanded view of the best-fit simulated and experimental sample cell pressure versus time curves in FIG. 5.

Eq. 10 is the diffusion equation inside a spherical particle. Other particle geometries, e.g., slab, cube, rectangular cube, etc., can be similarly solved to give simulated uptake curves. FIG. 6 shows for this example the simulated uptake curve after the optimization of the diffusion coefficient parameter to give the best fit with the measured uptake curve. The best fit curve was obtained with a cube geometry for the particle and the value of the diffusion coefficient parameter that gave this simulated uptake was $0.70 \times 10^{-16}$ m$^2$s$^{-1}$. In this example, the curve fitting was performed visually, that is, the curves were compared by eye and the operator decides which curve gave the best fit. Other methods to optimize the diffusion coefficient can also be used.

What is claimed is:

1. A method for measuring a molecular diffusion coefficient in a porous powder comprising:
   (a) providing a gas flow control means in communication by conduit with a supply container at an inlet to said gas flow control means and in communication by conduit with a sample cell with a weighed amount of the porous powder at an outlet to said gas flow control means, further providing the supply container is of known volume in contact with a supply container temperature measuring means and in communication by conduit: with a supply container pressure measuring means, by valving with at least one gas supply, and by valving with a vacuum pump assembly, and further providing the sample cell is of known volume in contact with a sample cell temperature measuring means at a conduit to the sample cell and in communication by conduit: with a sample cell pressure measuring means and by valving with a vacuum pump assembly, and placing the sample cell in a constant temperature bath;
   (b) determining a curve of sample cell pressure versus time further comprising treating the porous powder into a known chemical state, keeping the constant temperature bath at a fixed temperature, evacuating by vacuum pump assembly the supply container and sample cell and then isolating the supply container and sample cell, and supplying a gas to the supply container, then using the gas flow control means to allow communication between the supply container and the sample cell for a period between one to thirty seconds, and measuring the pressure and temperature in the supply container and the pressure and temperature in the sample cell as a function of time;
   (c) calculating a curve of sample cell pressure versus time to fit the curve obtained in step (b) further comprising using numerical analysis means to provide a computer program comprising a mass balance equation of the sample cell with the diffusion coefficient as a parameter, and using a computer with the computer program and an estimated value of the diffusion coefficient and the measured pressure, temperature and volume of the supply container and measured volume, temperature and weight of powder in the sample cell to compute said curve of sample cell pressure versus time;
   (d) repeating the computation in step (c) thereby to optimize the diffusion coefficient parameter by finding the best fit between the computed curve of sample cell pressure versus time and the corresponding curve measured in step (b), and using the optimized diffusion coefficient as the measured diffusion coefficient.

2. The method of claim 1 for measuring a molecular diffusion coefficient in a porous powder, further comprising repeating steps (b) to (d) until the pressure in the sample cell has reached a pressure beyond which no additional gas uptake occurs in the porous powder to get the diffusion coefficient in different pressure ranges, wherein the supplying of the gas to the supply container can be omitted if the supply container pressure is higher than the sample cell pressure.

3. The method of claim 1 for measuring a molecular diffusion coefficient in a porous powder, further comprising using the gas flow control means to allow communication between the supply container and the sample cell for less than twenty seconds.

4. The method of claim 1 for measuring a molecular diffusion coefficient in a porous powder, further comprising providing pressure measuring means with a precision of less than 0.3% of the reading for measuring the pressure in the supply container and the pressure in the sample cell.

5. The method of claim 1 for measuring a molecular diffusion coefficient in a porous powder, further comprising providing for the diffusion coefficient parameter in the computer program to be a function of a space variable in the porous powder.

6. The method of claim 1 for measuring a molecular diffusion coefficient in a porous powder, further comprising measuring an adsorption isotherm of the gas and using this in the computer program.

7. A method for measuring a molecular diffusion coefficient in a porous powder comprising:
   (a) providing a gas flow control means in communication by conduit with a supply container at an inlet to said gas flow control means and in communication by conduit with a sample cell with a weighed amount of the porous powder at an outlet to said gas flow control means, further providing the supply container is of known volume in contact with a supply container temperature measuring means and in communication by conduit: with a supply container pressure difference measuring means, by valving with at least one gas supply, and by valving with a vacuum pump assembly, and further providing the sample cell is of known volume in contact with a sample cell temperature measuring means at a conduit to the sample cell and in communication by conduit: with a sample cell pressure measuring means and by valving with a vacuum pump assembly, and placing the sample cell in a constant temperature bath;
   (b) determining a curve of sample cell pressure versus time further comprising treating the porous powder into a known chemical state, keeping the constant temperature bath at a fixed temperature, evacuating by vacuum pump assembly the supply container and sample cell and then isolating the supply container and sample cell, and supplying a gas to the supply container, then using the gas flow control means to allow communication between the supply container and the sample cell for a period between one second to thirty seconds, and measuring the pressure and temperature in the supply container and the pressure and temperature in the sample cell as a function of time, further comprising providing the supply container pressure difference measuring means comprises a reference chamber with a constant pressure in contact with a reference chamber temperature measurement means and a pressure difference measuring means with a precision of less than 0.3% of the reading that has its high pressure connection in communication with the reference chamber and its low pressure connection in communication with the supply container;

(c) calculating a curve of sample cell pressure versus time to fit the curve obtained in step (b) further comprising using numerical analysis means to provide a computer program comprising a mass balance equation of the sample cell with the diffusion coefficient as a parameter, and using a computer with the computer program and an estimated value of the diffusion coefficient and the measured pressure, temperature and volume of the supply container and measured volume, temperature and weight of powder in the sample cell to compute said curve of sample cell pressure versus time;

(d) repeating the computation in step (c) thereby to optimize the diffusion coefficient parameter by finding the best fit between the computed curve of sample cell pressure versus time and the corresponding curve measured in step (b), and using the optimized diffusion coefficient as the measured diffusion coefficient.

8. The method of claim 7 for measuring a molecular diffusion coefficient in a porous powder, further comprising repeating steps (b) to (d) until the pressure in the sample cell has reached a pressure beyond which no additional gas uptake occurs in the porous powder to get the diffusion coefficient in different pressure ranges, wherein the supplying of the gas to the supply container can be omitted if the supply container pressure is higher than the sample cell pressure.

9. The method of claim 7 for measuring a molecular diffusion coefficient in a porous powder, further comprising using the gas flow control means to allow communication between the supply container and the sample cell for a period less than twenty seconds.

10. The method of claim 7 for measuring a molecular diffusion coefficient in a porous powder, further comprising providing pressure measuring means with a precision of less than 0.3% of the reading for measuring the pressure in the sample cell.

11. The method of claim 7 for measuring a molecular diffusion coefficient in a porous powder, further comprising providing for the diffusion coefficient parameter in the computer program to be a function of a space variable in the porous powder.

12. The method of claim 7 for measuring a molecular diffusion coefficient in a porous powder, further comprising measuring an adsorption isotherm of the gas and using this in the computer program.

* * * * *